(12) United States Patent
Shong

(10) Patent No.: US 7,824,713 B1
(45) Date of Patent: Nov. 2, 2010

(54) METHOD FOR TREATING DIAPER RASH USING SUPERHYDRATED BACTERIOSTATIC TOPICAL PREPARATION WITH STABLE ACID PH

(76) Inventor: Wallace W. Shong, 201 Buckman St., Augusta, WI (US) 54722

( * ) Notice: Subject to any disclaimer, the term of this patent is extended or adjusted under 35 U.S.C. 154(b) by 777 days.

(21) Appl. No.: 11/810,680

(22) Filed: Jun. 7, 2007

(51) Int. Cl.
- *A61K 33/22* (2006.01)
- *A61K 33/30* (2006.01)
- *A61K 47/14* (2006.01)
- *A61K 47/44* (2006.01)
- *A61K 31/718* (2006.01)
- *A61P 17/00* (2006.01)

(52) U.S. Cl. .................. 424/642; 424/659; 514/778; 514/785; 514/786; 514/865; 514/928; 514/969

(58) Field of Classification Search .................. 424/642, 424/659; 514/865, 778, 785, 786, 928, 969
See application file for complete search history.

(56) References Cited

U.S. PATENT DOCUMENTS

| | | |
|---|---|---|
| 4,382,919 A | 5/1983 | Alonso |
| 4,556,560 A | 12/1985 | Buckingham |
| 5,091,193 A | 2/1992 | Enjoiras |
| 5,194,261 A | 3/1993 | Pechierri |
| 5,362,488 A | 11/1994 | Sibley et al. |
| 6,589,537 B2 | 7/2003 | Harbeck |
| 6,803,045 B1 | 10/2004 | Goldberg |
| 6,855,326 B2 | 2/2005 | Palumbo et al. |
| 6,911,196 B2 * | 6/2005 | Hamtini ................... 424/78.08 |
| 7,655,717 B2 * | 2/2010 | Goulbourne ................ 524/400 |

* cited by examiner

*Primary Examiner*—John Pak
(74) *Attorney, Agent, or Firm*—Robert T. Johnson

(57) ABSTRACT

A method for treating diaper rash, leg ulcers and bed sores using super hydrated bacteriostatic topical preparation with a stable acid pH 5.82, by applying this topical application, which is a mixture of anhydrous lanolin (USP), water, boric acid powder (USP), edible corn starch, white petrolatum, cosmetic grade, and zinc oxide ointment (USP 20% zinc oxide) mixed in a paddle mixer at a temperature of about 100° F. to 107° F. then applying topically, the super hydrated bacteriostatic preparation, at room temperature, on the rash, leg ulcers, or bed sores.

3 Claims, No Drawings

METHOD FOR TREATING DIAPER RASH USING SUPERHYDRATED BACTERIOSTATIC TOPICAL PREPARATION WITH STABLE ACID PH

BACKGROUND OF THE INVENTION

A skin rash is a very common, particularly in diapered individuals, including neonates, babies and adults. There has been much study and effort to date to eliminate this problem and present studies indicate that in many cases the rash is due to a yeast/bacterial growth in a neutral or alkaline environment and by lowering the pH along with a mild antiseptic, in an aqueous environment, stops the yeast/bacterial growth.

The term "rash" may include:
RASH—An eruption on the body with no elevation on the skin.
ULCER—necrosis of epithelial tissue.
BED SORE—Decubitus ulcer; ulceration of tissue covering prominent bony parts of the skin.
EXANTHEM—Skin rash; ulcer
DIAPER RASH—Condition caused by excessive urinary ammonia.

OBJECTS OF THIS INVENTION

An object of this invention is to create a topical preparation, in an aqueous environment among components that are aquaphobic, which is accomplished by super-hydrating lanolin (wool fat) to create an environment that approximates ten percent water

SUMMARY OF THE INVENTION

This invention for a method to cure a rash, particularly a diaper rash, leg ulcers, and bed sores, is aimed at having an acid environment at a pH of about 5.82, having a range of from pH 5 to pH 6, and including boric acid as a bacteriostat to create and maintain an acid environment, or mantle of pH 5.82, in an aqueous environment to increase the rate of epithelial cell regeneration, as epithelial cells regenerate more rapidly in a wet environment than in a dry environment.

SUBJECT MATTER RELATED AS BACKGROUND INFORMATION

6,803,045 for TREATING DIAPER RASH.
6,855,326 for SKIN PROTECTION COMPOSITION.
6,627,178 for—TREATING DIAPER RASH.
6,589,537 for INFANT SKIN CARE COMPOSITION.
5,362,488 for BUFFERED DIAPER RASH CREAM.
5,194,261 for DIAPER RASH TREATMENT.
5,091,193 for DIAPER RASH TREATMENT AND COMPOSITIONS.
4,556,560 for—TREATMENT—DIAPER RASH ETC.
4,382,919 for COMPOSITION FOR—MALODOROUS SKIN

DETAILED DESCRIPTION OF THE INVENTION

This present application is for a salve for treatment of diaper rash, leg ulcers and bed sores, and includes an aqueous mantle of water dispersed in anhydrous lanolin, with addition of boric acid plus addition of zinc oxide ointment USP; (20% zinc oxide) plus edible corn starch, plus white cosmetic grade petrolatum.

The water or aqueous/acid mantle is of major importance and is attained by addition of 200 cc water to 300 grams of anhydrous lanolin, and mixing in a paddle mixer at a temperature range of 38° C.-42° C. equal to 100° F.-107° F., then add 50 grams of boric acid (USP) to the water—lanolin mix followed by 454 grams of edible corn starch, 454 grams of white petrolatum (cosmetic grade) and 454 grams of zinc oxide ointment USP (20% zinc oxide), mix all ingredients together in paddle mixer.

The pH of the final mix is about 5.82, and with the aqueous/acid mantle is suited for curing a rash, and protecting skin from developing a diaper rash.

The method of preparation of this salve is critical, and is not merely mixing the ingredients but includes special steps' of adding warm water at about 100° F. to 107° F. to anhydrous lanolin (USP) and mixing in a paddle mixer to obtain water saturation of the anhydrous lanolin then boric acid powder (USP) grade is added to the anhydrous lanolin—water mix and dispersed therein by the mixing apparatus, then edible corn starch is added, mixed into the anhydrous lanolin-water boric acid (USP) mix, and further mixed in the mixing apparatus and white petrolatum (cosmetic grade) is added to the anhydrous lanolin plus water plus boric acid (USP) plus edible starch plus white petrolatum (cosmetic grade) is added and mixing continued plus zinc oxide ointment (USP 20% zinc oxide) is added and mixing continued to attain a thorough mixture. All the mixing of the ingredients to be at, or about 100°-107° F. for good dispersion of the components of this topical preparation The ingredient list, expressed as parts, of the topical preparation of this invention is shown below:

| INGREDIENT | AMOUNT EXPRESSED AS PARTS BY WEIGHT |
| --- | --- |
| ANHYDROUS LANOLIN (USP) | 300 |
| WATER | 200 |
| BORIC ACID POWDER (USP) | 50 |
| CORN STARCH (EDIBLE) | 454 |
| WHITE PETROLATUM (COSMETIC GRADE) | 454 |
| ZINC OXIDE OINTMENT (USP) (20% ZINC OXIDE) | 454 |

Function of Ingredients

Zinc oxide (USP) 20% zinc oxide, is an astringent and a protectent.

Boric acid is bacteriostatic and creates an acid environment with a pH of 5.82. which helps to establish an acid mantle, and in the case of urinary incontinence it neutralizes the generated ammonia.

Corn starch is an absorbent and a lubricant.

Super hydrated lanolin (wool fat) creates an aqueous environment (at about 10% water) with the other ingredients that are aquaphobic.

Having described my invention, I claim:

1. A method for treatment of diaper rash, leg ulcers or bed sores comprising:
    (a) preparing a super hydrated bacteriostatic topical preparation mixture with a stable acid pH of about 5.82 by
        (i) adding and mixing 200 parts by weight of warm water at a temperature of about 100° F. to 107° F. to 300 parts by weight of anhydrous lanolin (USP),
        (ii) adding and mixing boric acid powder (USP),
        (iii) adding and mixing edible corn starch powder, (iv) adding and mixing white petrolatum (cosmetic grade), and (v) adding and mixing zinc oxide ointment (USP) (20% zinc oxide);

wherein all of the mixing steps are carried out at a temperature of about 100° F. to 107° F.; and (b) applying as a mantle said bacteriostatic topical preparation mixture, at room temperature, to said diaper rash, leg ulcers or bed sores.

2. The method of claim 1, wherein said bacteriostatic topical preparation mixture consists of:

(i) 300 parts by weight anhydrous lanolin (USP);

(ii) 200 parts by weight water;

(iii) 50 parts by weight boric acid powder (USP);

(iv) 454 parts by weight edible corn starch powder; and (v) 454 parts by weight zinc oxide ointment (USP) (20% zinc oxide).

3. The method of claim 1, wherein said bacteriostatic topical preparation mixture is prepared by mixing the ingredients of said mixture in a paddle mixer at a temperature of about 100° F. to 107° F.

* * * * *

UNITED STATES PATENT AND TRADEMARK OFFICE
CERTIFICATE OF CORRECTION

| | | |
|---|---|---|
| PATENT NO. | : 7,824,713 B1 | Page 1 of 1 |
| APPLICATION NO. | : 11/810680 | |
| DATED | : November 2, 2010 | |
| INVENTOR(S) | : Wallace W. Shong | |

It is certified that error appears in the above-identified patent and that said Letters Patent is hereby corrected as shown below:

Title Page item 76 should read  WALLACE W. SHONG
3338 BRIARCREST DR.
EAU CLAIRE, WIS. 54701

Signed and Sealed this

Twenty-eighth Day of December, 2010

David J. Kappos
*Director of the United States Patent and Trademark Office*